United States Patent
Wu et al.

(10) Patent No.: US 7,622,702 B2
(45) Date of Patent: Nov. 24, 2009

(54) POWER CONTROLLING APPARATUS APPLIED TO BIOCHIP AND OPERATING METHOD THEREOF

(75) Inventors: Chung-Yu Wu, Hsinchu (TW); Po-Kang Lin, Taipei (TW); Li-Ju Lin, Hsinchu (TW); Wen-Chia Yang, Hsinchu (TW); Chen Wan, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 65 days.

(21) Appl. No.: 12/129,237

(22) Filed: May 29, 2008

(65) Prior Publication Data

US 2009/0066389 A1    Mar. 12, 2009

(30) Foreign Application Priority Data

Sep. 12, 2007    (TW) ............................... 96134044 A

(51) Int. Cl.
*A61F 2/14* (2006.01)
*H03H 11/16* (2006.01)
(52) U.S. Cl. ....................... 250/214 R; 607/54; 607/61; 607/72; 623/6.63
(58) Field of Classification Search ............. 250/214 R; 607/54, 61, 72; 623/6.63
See application file for complete search history.

(56) References Cited

U.S. PATENT DOCUMENTS

| | | | | |
|---|---|---|---|---|
| 6,393,327 | B1 * | 5/2002 | Scribner | 607/54 |
| 6,647,297 | B2 * | 11/2003 | Scribner | 607/54 |
| 6,976,998 | B2 * | 12/2005 | Rizzo et al. | 623/6.63 |
| 2004/0172100 | A1 * | 9/2004 | Humayun et al. | 607/54 |
| 2006/0184245 | A1 * | 8/2006 | Graf et al. | 623/6.63 |
| 2008/0294224 | A1 * | 11/2008 | Greenberg et al. | 607/54 |
| 2009/0066389 | A1 * | 3/2009 | Wu et al. | 327/259 |

\* cited by examiner

*Primary Examiner*—John R Lee
(74) *Attorney, Agent, or Firm*—Morris, Manning & Martin LLP; Tim Tingkang Xia

(57) ABSTRACT

The invention discloses a power controlling apparatus for a biochip including M regions. Each region includes a plurality of cells respectively. The power controlling apparatus includes a pulse generating module, a combinational circuit, and M controlling modules. The pulse generating module generates a pulse. The combinational circuit receives the pulse and generates M controlling signals. Each controlling signal has a predetermined phase which is different from the phase of the other controlling signal. The M controlling modules are electrically connected to the combinational circuit. Each of the M controlling signals corresponds to and activates one of the M controlling modules to selectively power on one corresponding region of the M regions. The cells in the corresponding region which is powered have an action potential refractory time that is longer than the power-on interval of the corresponding region.

11 Claims, 6 Drawing Sheets

_US 7,622,702 B2_

POWER CONTROLLING APPARATUS APPLIED TO BIOCHIP AND OPERATING METHOD THEREOF

BACKGROUND OF THE INVENTION

1. Field of the Invention

The invention relates to power control, and particularly, to a power controlling apparatus applied to a biochip and the operating method thereof.

2. Description of the Prior Art

Vision loss is a serious medical issue, where retinal diseases play major roles. For example, retinitis pigmentosa is a genetic disease. It is estimated that 1.5 to 6 out of every 10 thousand people are sick with this disease. The onset age of this disease ranges from 10 to 45 years old. The symptom of this disease is night blindness or sight-shrink. A majority of people with this disease become legally blind by the age of forty. At present, there is no effective treatment for retinitis pigmentosa.

Because of the rapid development of bio-technology in recent years, various biochips have given a ray of hope to the patients sick with the diseases hard to be cured. Considering the safety of the patients, a treatment called sub-retinal silicon chip implantation will be relatively safer and less-damaging to the eye structure of the patients receiving this treatment compared to other possible treatments for this disease.

However, the retinal chip used in the sub-retinal silicon chip implantation treatment is generally powered by solar-cells. The most serious drawback is that the photo-current generated by solar-cells is small and the efficiency of the solar-cell could not be effectively improved. Therefore, the solar-cell powered retinal chip will be limited by the small photo-current and cannot reach higher output power.

Therefore, the invention provides a power controlling apparatus applied to a biochip and the operating method thereof to solve the above problems.

SUMMARY OF THE INVENTION

The invention provides a power controlling apparatus applied to a biochip and the operating method thereof. An embodiment according to the invention is a power controlling apparatus applied to a biochip.

The biochip includes M regions (M is a positive integer), and each of the M regions includes a plurality of cells respectively. The power controlling apparatus includes a pulse generating module, a combinational circuit, and M controlling modules.

The pulse generating module is used for generating a pulse. The combinational circuit receives the pulse and generates M controlling signals. Each controlling signal has a predetermined phase which is different from the phases of the other controlling signals. The M controlling modules are electrically connected to the combinational circuit. Each of the M controlling signals corresponds to one of the M controlling modules and activates that controlling module to selectively power on one of the M regions corresponding to that controlling module. The cells in the corresponding region which are powered have an action potential refractory period which is longer than the power-on interval of the corresponding region.

Compared to the prior art, the power controlling apparatus applied to a biochip disclosed by the invention enables the feasibility of solar cell powered-only sub-retinal chip that prevents the damage of eyeball structure caused by the conventional artificial retina chip. For example, the damage may be caused by winding through the eyeball or providing the power by wiring in the eyeball with the RF wireless transmission. The safety of the artificial retina chip implantation will be enhanced. In addition, combined with its characteristic of action potential refractory period, the output efficiency of the artificial retina chip will be improved by taking turns to provide power to divided region controlled by the circuit.

The advantage and spirit of the invention may be understood by the following recitations together with the appended drawings.

BRIEF DESCRIPTION OF THE APPENDED DRAWINGS

DETAILED DESCRIPTION OF THE INVENTION

Figure 1:
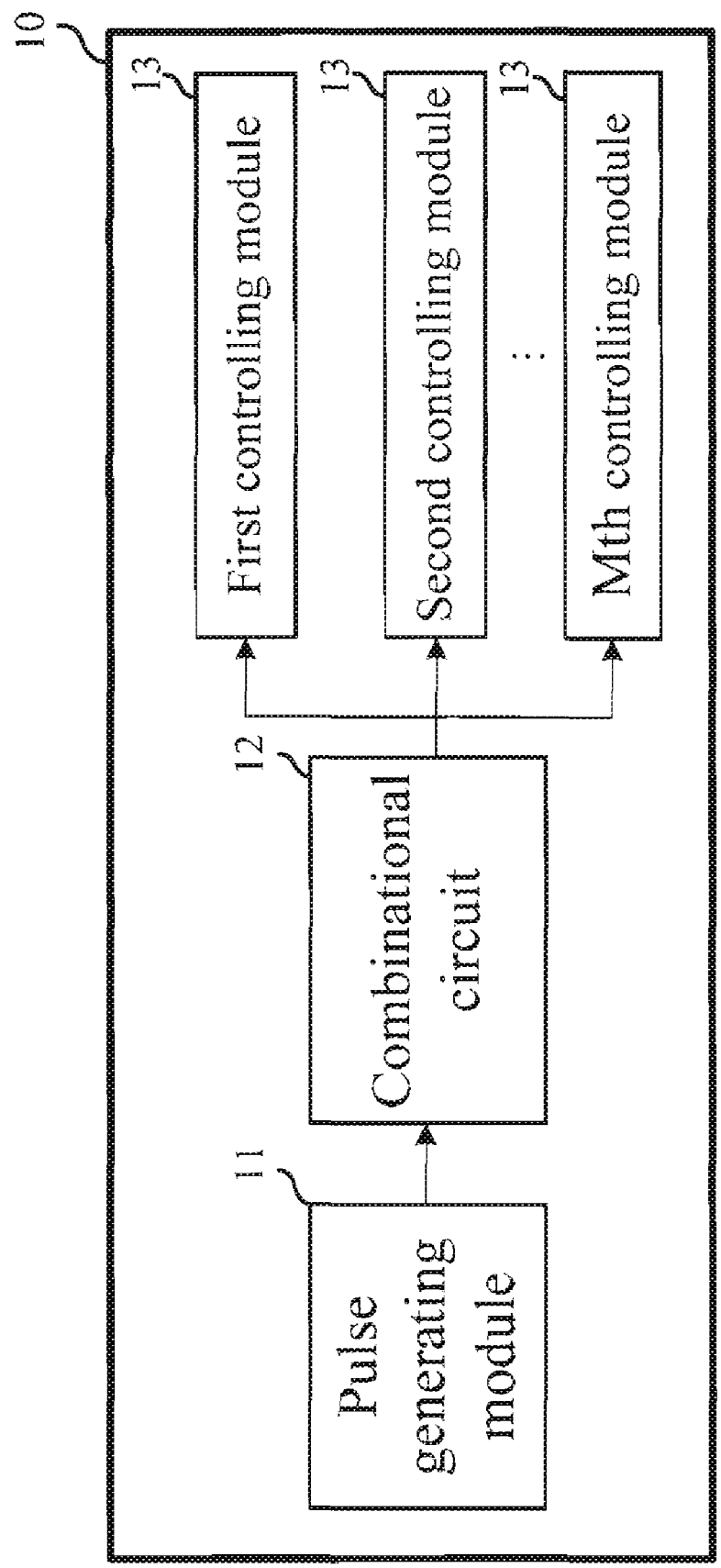
FIG. 1 shows the functional block diagram of the power controlling apparatus applied to a biochip in the first embodiment of the invention.

The first embodiment according to the invention is a power controlling apparatus applied to a biochip. The biochip includes M regions (M is a positive integer), and each of the M regions includes a plurality of cells respectively. Please refer to FIG. 1. FIG. 1 shows the functional block diagram of the power controlling apparatus in the first embodiment. As shown in FIG. 1, the power controlling apparatus 10 includes a pulse generating module 11, a combinational circuit 12, and M controlling modules 13.

Figure 2:
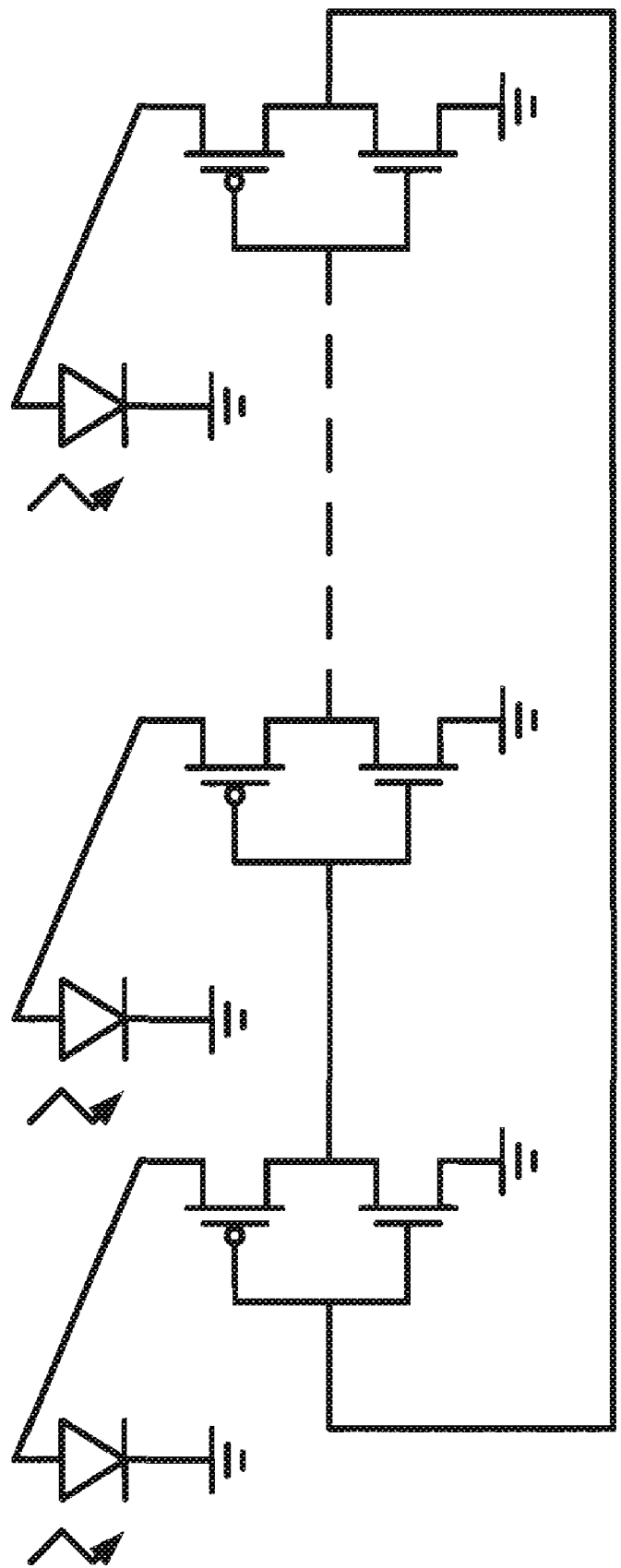
FIG. 2 shows the circuit diagram of the ring oscillating circuit.

The pulse generating module 11 is used for generating a pulse. In practical applications, the pulse generating module 11 can be a ring oscillating circuit, as shown in FIG. 2. The combinational circuit 12 is electrically connected to the pulse generating module 11. The combinational circuit 12 receives the pulse and generates M controlling signals. Each of the M controlling signals has a different phase from the phases of the other controlling signals.

The M controlling modules 13 are electrically connected to the combinational circuit 12. Each of the M controlling signals corresponds to one of the M controlling modules and activates that controlling module to selectively power on one of the M regions corresponding to that controlling module.

In practical applications, the electrical power for the corresponding region can be provided by solar-cells. It is not necessary to use an external power source or the destructive way of winding or wiring for operating the biochip. Therefore, the safety of the patients under the treatment or after the treatment will be highly improved, and the risk of the patients will be lowered to the minimum.

When the corresponding region of the biochip is powered on, the cells in the corresponding region will be triggered. The triggered cells in the corresponding region have an action potential refractory period. The cells will be irresponsive to any stimulus during a period of time once the cells are triggered, and this period of time is called the action potential refractory period. Stimulating the cell continuously in this period is a waste. Therefore, triggering the cells with periodic pulses provides a way to save power.

In practical applications, only one region of the M regions is powered on and the other regions are powered off. That is to say, among all regions of the biochip, only one region is powered on at a certain time. This is a way of taking turns to provide power to divided regions, not only the unnecessary power waste can be saved according to the characteristic of cells, but also the output efficiency obtained by each region of the biochip will be highly improved respectively.

As long as the interval of power-on time of the corresponding region is kept shorter than the action potential refractory period, the way of taking turns to provide power for all regions can be used in the invention to save power and boost the output power of each region. For example, if a biochip is divided into M regions and the power-on times of the M regions are all different, the effect of taking turns to trigger the cells will be the same as that of continuously triggering the cells. Since the supply power is shared by all regions in the latter approach and only by a single region in the former, the efficiency will have M times improvement by adopting the former approach.

Figure 3:
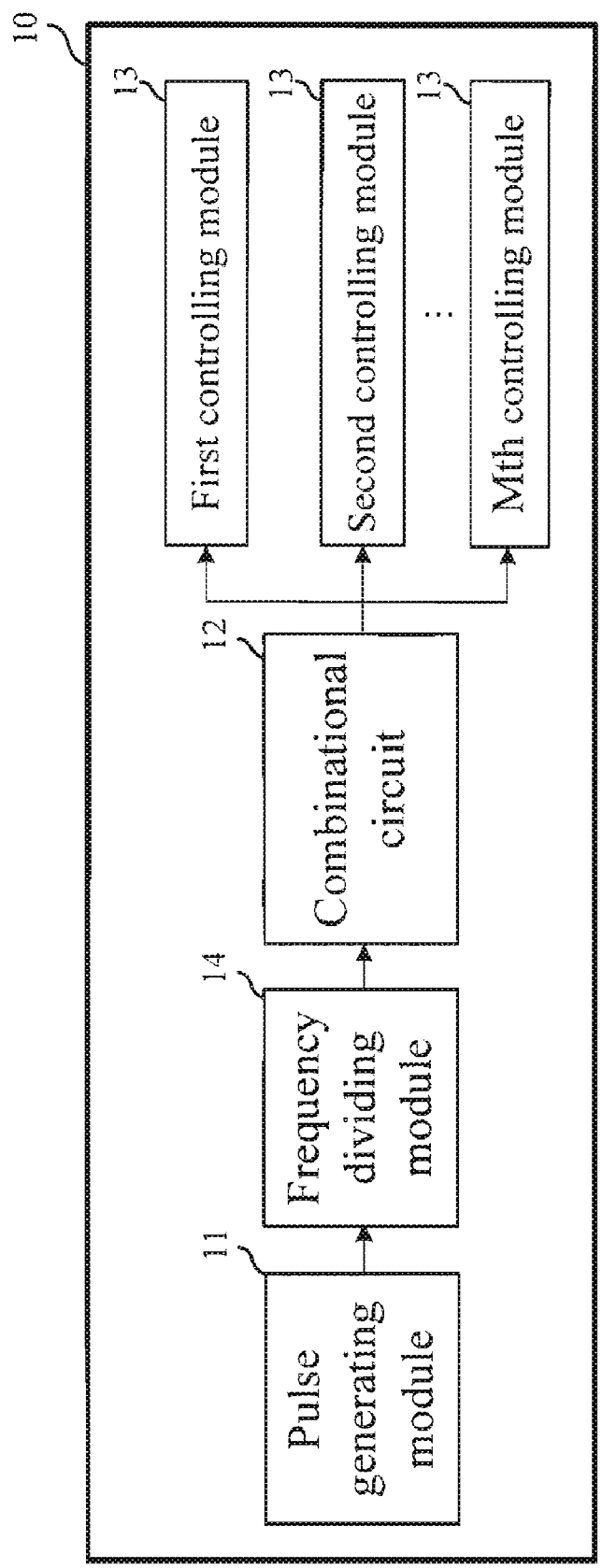
FIG. 3 shows the functional block diagram of the power controlling apparatus shown in FIG. 1 further including a frequency dividing module.

In practical applications, the power controlling apparatus 10 can further include a frequency dividing module 14, as shown in FIG. 3. The frequency dividing module 14 is electrically connected to the pulse generating module 11, and used for dividing the frequency of the pulse to meet the needs of the combinational circuit 12.

In addition, the combinational circuit 12 can be a logic circuit. The logic circuit can include digital logic gates, for example, a NAND logic gate, a NOR logic gate, or an inverter gate.

Figure 4:
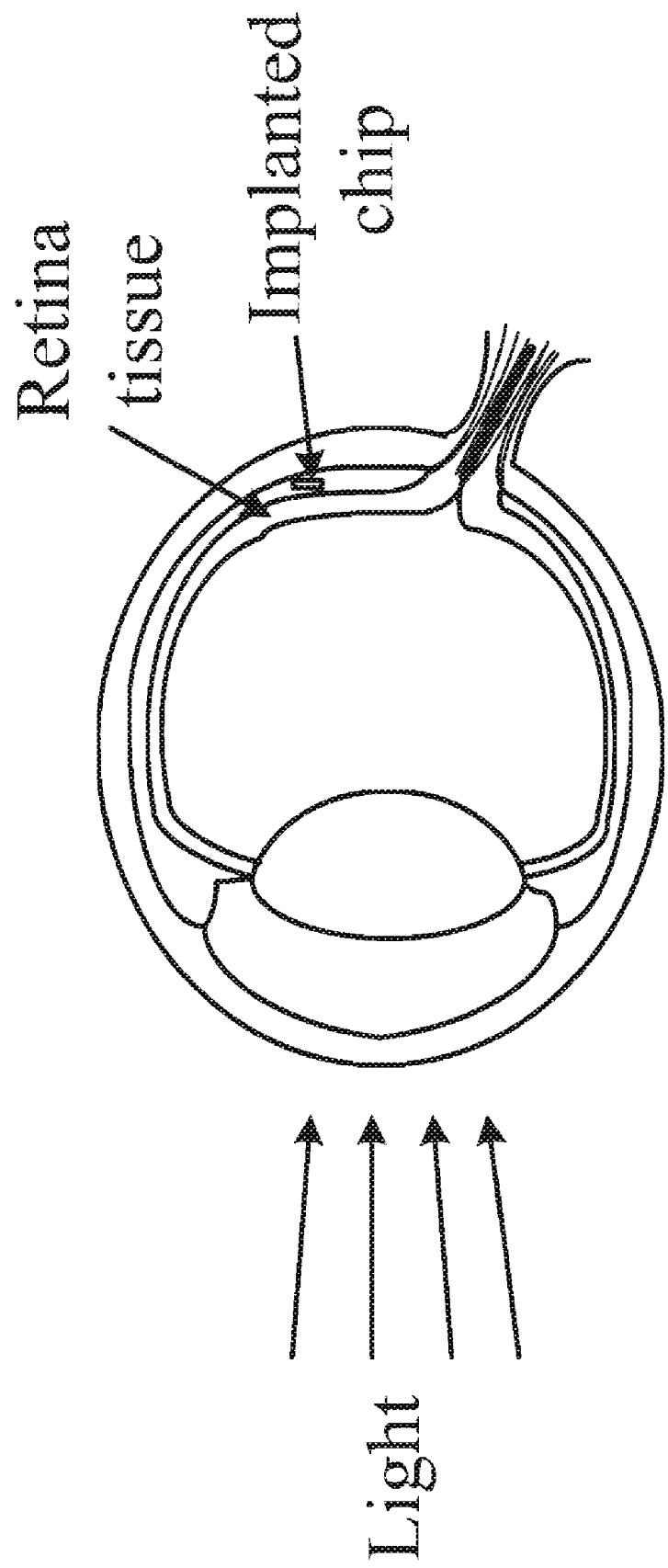
FIG. 4 shows the position the biochip implanted into the sub-retinal area of the eyeball.

In practical applications, the biochip can be an artificial retina chip. After the manufacturing process, the artificial retina chip can be used as an implanted biomedical device. When a sub-retinal silicon chip implantation treatment is performed to a patient sick with retinal disease, the implanted biochip can be implanted into the sub-retinal region of the eye of the patient through surgery. The exact position of the implanted chips can be adjusted according to surgical situation. Please refer to FIG. 4. FIG. 4 shows the position of the retinal chip which is implanted into the sub-retinal area of the eye.

Figure 5:
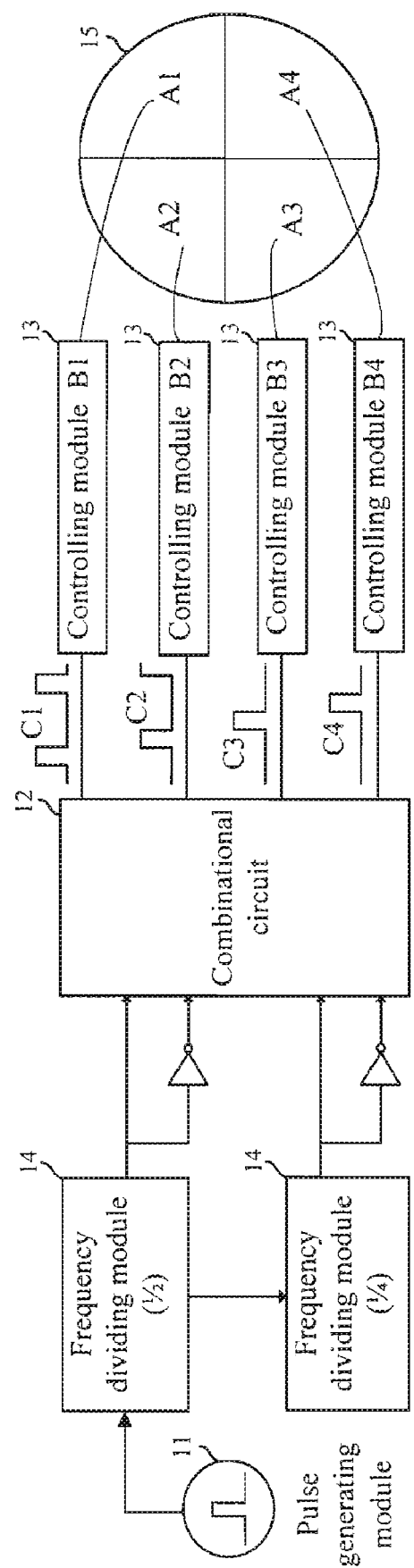
FIG. 5 shows an example of applying the power controlling apparatus of the invention to an artificial retina chip.

An example is shown in FIG. 5 in which an artificial retina chip 15 is divided into four regions A1~A4. Regions A1~A4 correspond to the four controlling modules B1~B4 of the power controlling apparatus 10 applied to the artificial retina chip 15 respectively. After the pulse generating module 11 generates a reference pulse, the combinational circuit 12 will generate four controlling signals C1~C4 with different phases according based on the pulses. The controlling modules B1~B4 correspond to the controlling signals C1~C4 respectively. The controlling module B1 uses the controlling signal C1 to control the power on/off of the region A1 of artificial retina chip 15. The controlling module B2 uses the controlling signal C2 to control the power on/off of the region A2 of artificial retina chip 15. The controlling modules B3 and B4 are similar to B1 and B2, so they will not be repeated here.

The second embodiment according to the invention is a power controlling apparatus operating method. The power controlling apparatus is applied to a biochip. The biochip includes M regions (M is a positive integer) and each of the M regions includes a plurality of cells.

Figure 6:
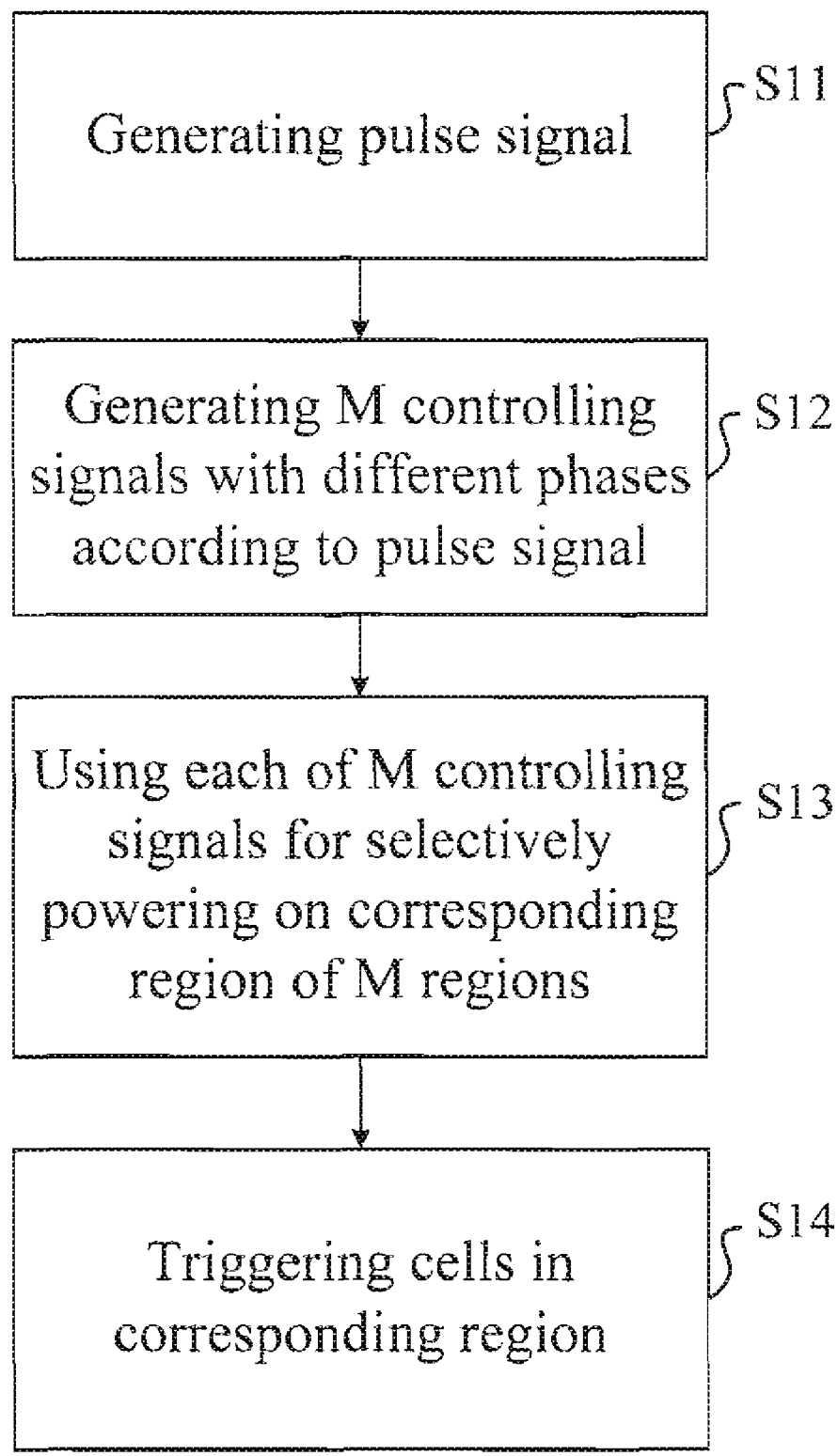
FIG. 6 shows the flowchart of the power controlling apparatus operating method applied to a biochip in the second embodiment of the invention.

Please refer to FIG. 6. FIG. 6 shows the flowchart of the power controlling apparatus operating method in the second embodiment. Firstly, step S11 is performed to generate a pulse. Then, step S12 is performed for generating M controlling signals with different phases according to the pulse. Each controlling signal has a different phase from the phases of other controlling signals.

Afterward, step S13 is performed to use each of the M controlling signals for selectively powering on a corresponding region of the M regions. When the corresponding region is powered on, step S14 is performed for triggering the cells in the corresponding region. The cells in the corresponding region which are powered have an action potential refractory period that is longer than the interval of power-on time of the corresponding region.

In practical applications, when the corresponding region of the M regions is powered on and the others of the M regions are powered off, the step of dividing the frequency of the pulse can be performed between step S11 and step S12.

Compared to the prior art, the power controlling apparatus applied to a biochip disclosed by the invention prevents the damage on eyeball structure caused by the conventional artificial retina chip. For example, the damage may be caused by winding through the eyeball or providing power by wiring in the eyeball with the RF wireless transmission. So the safety of the artificial retina chip implantation will be highly enhanced by the power controlling apparatus disclosed in the invention. In addition, combined with the characteristic of action potential refractory period, the output efficiency of the artificial retina chip will be improved by way of taking turns providing power controlled by the circuit.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A power controlling apparatus applied to a biochip, the biochip comprising M regions, M being a positive integer, each of the M regions comprising a plurality of cells, the power controlling apparatus comprising:
   a pulse generating module, for generating a pulse;
   a combinational circuit receiving the pulse for generating M controlling signals, each controlling signal with a predetermined phase different from the phase of the other controlling signals; and
   M controlling modules electrically connected to the combinational circuit, each of the M controlling signals corresponding to and for activating one of the M controlling modules to selectively power on one corresponding region of the M regions;
   wherein the cells in the corresponding region which is powered have an action potential refractory period longer than an interval of a power-on time of the corresponding region.

2. The power controlling apparatus of claim 1, wherein only one region of the M regions is powered on and the other regions are powered off.

3. The power controlling apparatus of claim 1, further comprising:
   a frequency dividing module, electrically connected to the pulse generating module for dividing the frequency of the pulse.

4. The power controlling apparatus of claim 1, wherein the corresponding region includes solar cells to provide electrical power thereto.

5. The power controlling apparatus of claim 1, wherein the combinational circuit comprises a NAND logic gate, a NOR logic gate, or an inverter gate.

6. The power controlling apparatus of claim 1, wherein the biochip is an artificial retina chip.

7. A power controlling apparatus operating method for a biochip, the biochip comprising M regions, M being a positive integer, each of the M regions comprising a plurality of cells respectively, the power controlling apparatus operating method comprising the steps of:

generating a pulse;

generating M controlling signals according to the pulse, each controlling signal with a predetermined phase different from the phase of the other controlling signals; and using each of the M controlling signals for selectively powering on a corresponding region of the M regions;

wherein the cells in the corresponding region which is powered have an action potential refractory period longer than an interval of a power-on time of the corresponding region.

8. The power controlling apparatus operating method of claim 7, wherein only one region of the M regions is powered on and the others of the M region are powered off.

9. The power controlling apparatus operating method of claim 7, further comprising the step of:

dividing the frequency of the pulse.

10. The power controlling apparatus operating method of claim 7, wherein the corresponding region includes solar cells to provide electrical power thereto.

11. The power controlling apparatus operating method of claim 7, wherein the biochip is an artificial retina chip.

* * * * *